July 29, 1975 A. L. CORDES Plant Pat. 3,754

BLACK ASH TREE

Filed July 15, 1974

WITNESS

Roland J. Hoffert

INVENTOR

Ashur Cordes

By

July 29, 1975 A. L. CORDES Plant Pat. 3,754

BLACK ASH TREE

Filed July 15, 1974

WITNESS

Roland J. Hoffert

INVENTOR

Ashur Cordes

By

United States Patent

Plant Pat. 3,754

Patented July 29, 1975

1

3,754

BLACK ASH TREE

Ashur L. Cordes, Rte. 1, Box 44,
Beresford, S. Dak. 57004

Filed July 15, 1974, Ser. No. 488,535

Int. Cl. A01h 5/12

U.S. Cl. Plt.—51 1 Claim

The present invention relates to a new and distinct variety of black ash tree of the species botanically known as *Fraxinus nigra,* which was selected from a group of seedlings cultivated on property near Henning, Minn.

At the time of my invention of this new variety of black ash tree, I was cultivating part of a group of approximately 5,000 seedlings from seeds selected from parent trees grown in north central Minnesota. In the process of cultivation and care of these seedlings, my attention was attracted to one particular tree exhibiting a strinkingly upright and narrow habit of growth which distinguished it from others of the same species and varieties known to me.

Continued observation of this seedling and of the progeny derived therefrom by budding over a prolonged period of time fully confirmed the above-mentioned growth habit of my new seedling, as well as establishing other outstanding characteristics thereof. Together these characteristics, as briefly enumerated in the following summary, represent a unique and valuable combination distinguishing my new black ash tree from all other varieties of which I am aware:

1. An unsually upright narrow habit of growth, producing a crown essentially columnar in form having a gently rounded top;
2. A strong central leader with a dense branching habit;
3. Attractive and uniform foliage covering the tree from approximately 6–8 ft. above the ground to the top when grown in full sunlight; and
4. Sparse flowering and seed production.

Asexual reproduction of my new black ash variety, as performed by me by budding at Beresford, S. Dak., shows that the foregoing characteristics and distinctions are established and transmitted through succeeding propagations.

The accompanying drawing shows a typical specimen tree of my new variety of black ash tree, illustrating its characteristic habits of growth, in particular:

Figure 1:
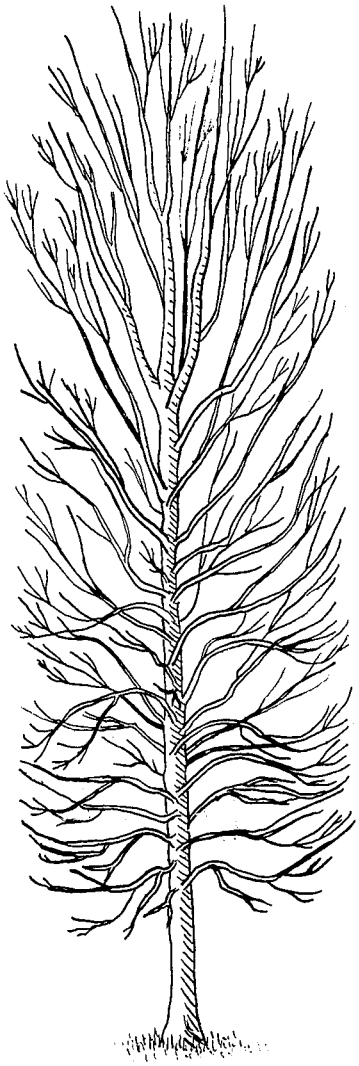
FIG. 1 shows a typical specimen of my new variety in a dormant condition.
Figure 2:
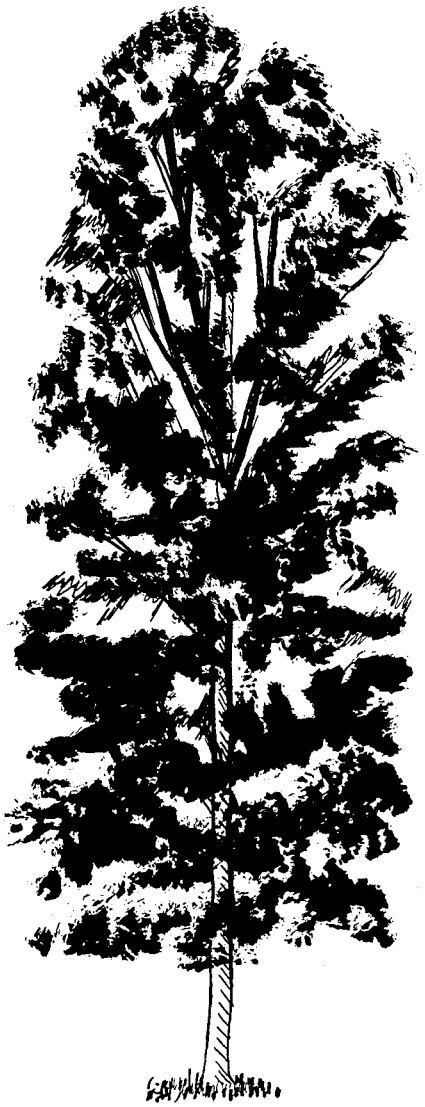
FIG. 2 shows the same specimen in full summer foliage.
Figure 1:
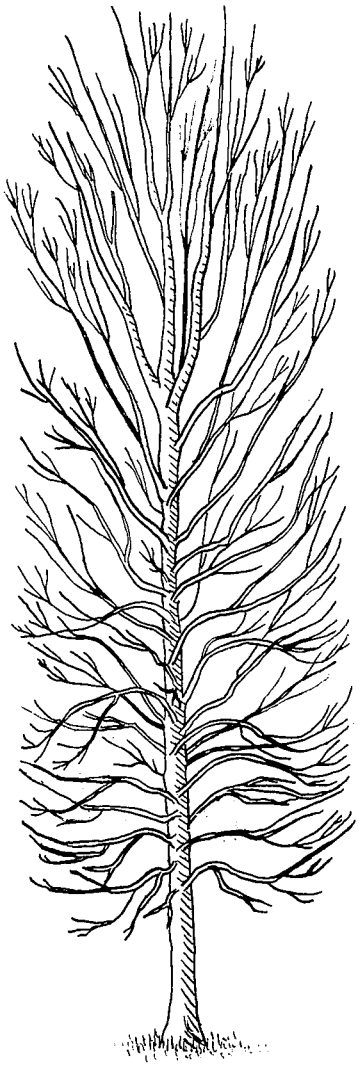
Figure 2:
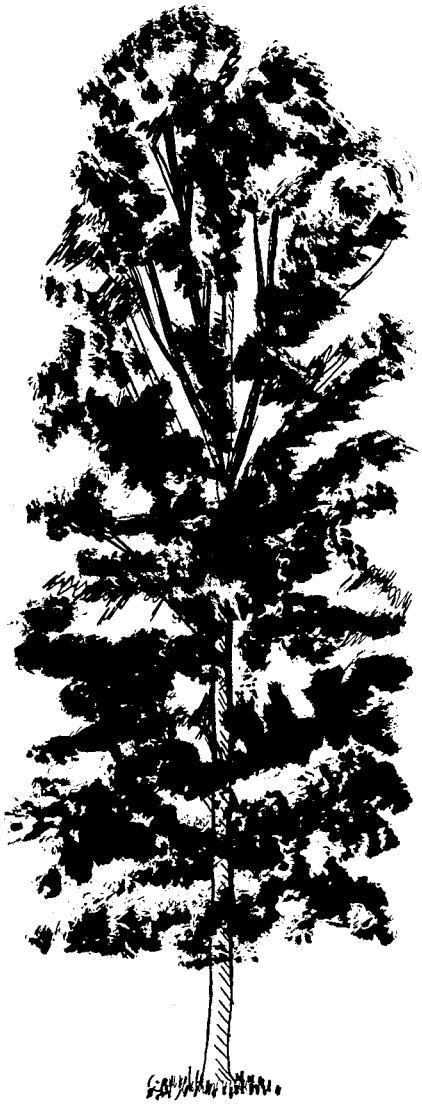

As shown in the drawing, the trunk or central leader of the tree is very erect and straight. At approximately two-thirds the overall height of the tree, an unusually large and strong leader and branch junction is formed by the central leader and auxiliary leaders or branches. This junction provides the tree with excellent strength and resistance to severe wind conditions. Below the midpoint of the tree, the branches consistently emerge from the central leader and extend generally horizontally outward. Above the midpoint, the branches successively turn gradually upward toward the topmost part of the crown, which is of a gently rounded form. The branches are uniformly spaced and the tree is essentially uniform in width from its lower branches to where its rounded topmost part begins to form. Only the lower 6–8 ft. of the central leader or trunk does not have these uniform branches.

2

The tree gives an indication of maturing at a height of approximately 60 ft. tall by approximately 15–18 ft. wide. Outward growth of branches is approximately slightly less than one-third the vertical growth of the tree in full sunlight.

The tree of my invention has shown an affinity for moist growing conditions, yet has also shown good tolerance to drought conditions. The tree has demonstrated an ability to put on a heavy wax coating on its leaves the growing season after drought conditions occur. This no doubt aids in moisture retention and increases its drought resistance.

Though the exceptionally right growth habit, columnar form, sparse seed production and uniform foliage of my new black ash variety are the principal distinctive features thereof, the following brief detailed description is given for convenience with color terminology in accordance with the Horticultural Colour Chart, copyright 1938 by R. F. Wilson and printed by Henry Stone & Son, Ltd., of Danbury, England, except where general color terms of ordinary dictionary significance are obvious:

Parentage: Seedling of undetermined parentage.

Propagation: Retains its distinguishing characteristics through succeeding propagations by budding.

Locality where grown and observed: Henning, Minn. and Beresford, S. Dak.

Tree: Medium size; tall (approximately 60 ft. indicated at maturity); width approximately ⅓ of overall height; narrow columnar head; hardy.

Trunk: Smooth, gray.

Branches: Slender, smooth, extending generally horizontally outward below the midpoint of the tree, with branches turning gradually upward in succession toward the topmost part of the crown.

*Color.*—New growth—Lettuce Green, No. 861/1, p. 176.

*Older branches.*—Brownish gray turning to grayish brown as branches age.

*Lenticels.*—Normal for the species.

Foliage: Leaf apparatus compound, 12 inches long by 10 inches wide; leaflets 5–6 inches long by 2–2½ inches wide.

*Shape.*—Oblong—lanceolate, rounded at the base.

*Margin.*—Serrate.

*Color.*—Upper side—Willow Green, No. 000862, p. 199.

*Under side.*—Lighter near Sage Green, No. 000861, p. 198.

*Fall color*—Amber.

Bloom: Blooms in mid-May in southern South Dakota, flowers sparse, may not flower each year.

Seeds: Sparse, seeds per bract usually in two's, rarely as many as four to five, often without seeds.

I claim:

1. A new and distinct variety of black ash tree of the species botanically known as *Fraxinus nigra,* substantially as herein shown and described, characterized particularly as to novelty by the unique combination of a distinctly upright and narrow habit of growth and columnar tree head, with a width approximately one-third its height when grown in full sunlight, uniform foliage, and sparse seed production.

No references cited.

ROBERT E. BAGWILL, Primary Examiner